(12) United States Patent
Wang

(10) Patent No.: US 11,589,453 B2
(45) Date of Patent: Feb. 21, 2023

(54) SYSTEM AND METHOD FOR RADIATION THERAPY

(71) Applicant: SHANGHAI UNITED IMAGING HEALTHCARE CO., LTD., Shanghai (CN)

(72) Inventor: Peng Wang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 51 days.

(21) Appl. No.: 17/131,903

(22) Filed: Dec. 23, 2020

(65) Prior Publication Data

US 2021/0120662 A1    Apr. 22, 2021

Related U.S. Application Data

(63) Continuation of application No. PCT/CN2019/092118, filed on Jun. 20, 2019.

(51) Int. Cl.
*H05H 7/00* (2006.01)
*A61N 5/10* (2006.01)
*H05H 7/08* (2006.01)

(52) U.S. Cl.
CPC .......... *H05H 7/08* (2013.01); *A61N 5/1077* (2013.01); *H05H 2007/084* (2013.01); *H05H 2007/087* (2013.01)

(58) Field of Classification Search
None
See application file for complete search history.

(56) References Cited

U.S. PATENT DOCUMENTS

| | | | |
|---|---|---|---|
| 6,111,932 A | 8/2000 | Dinsmore | |
| 2012/0229024 A1* | 9/2012 | Large | H01J 25/34 315/1 |
| 2013/0035905 A1* | 2/2013 | Constantin | H01J 3/029 703/1 |
| 2014/0031902 A1 | 1/2014 | Mashiach et al. | |
| 2016/0082251 A1 | 3/2016 | Moffitt et al. | |
| 2016/0243367 A1 | 8/2016 | Li et al. | |

OTHER PUBLICATIONS

International Search Report in PCT/CN2019/092118 dated Aug. 28, 2019, 6 pages.
Written Opinion in PCT/CN2019/092118 dated Aug. 28, 2019, 4 pages.

* cited by examiner

*Primary Examiner* — Dedei K Hammond
(74) *Attorney, Agent, or Firm* — Metis IP LLC

(57) ABSTRACT

A system and method for injecting an electron beam to an accelerator are provided. The system may include a cathode, an anode, and a modulation electrode. The cathode, for generating the electron beam, may have a first electrical potential. The anode may have a second electrical potential. The modulation electrode, located between the cathode and the anode, may be configured to adjust at least one parameter of the electron beam. The at least one parameter of the electron beam may include at least one transverse parameter of the electron beam.

19 Claims, 7 Drawing Sheets

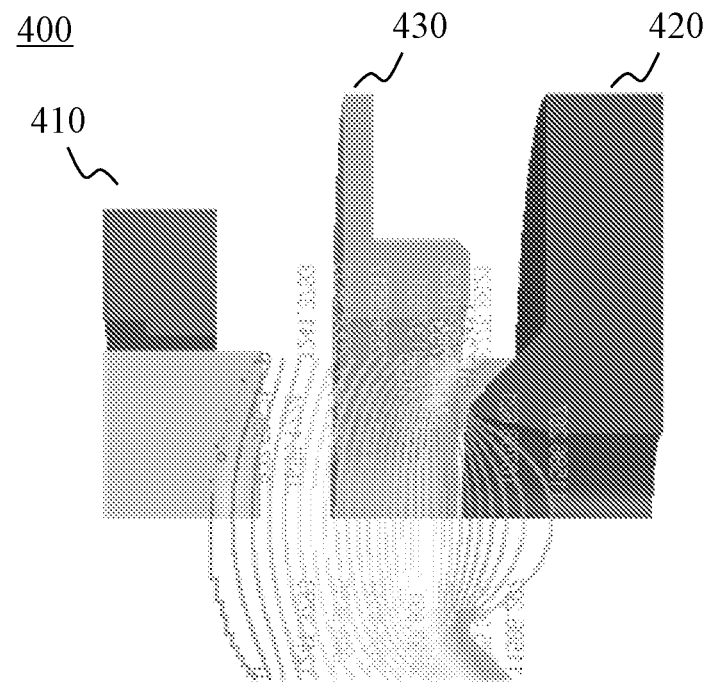
FIG. 4-A
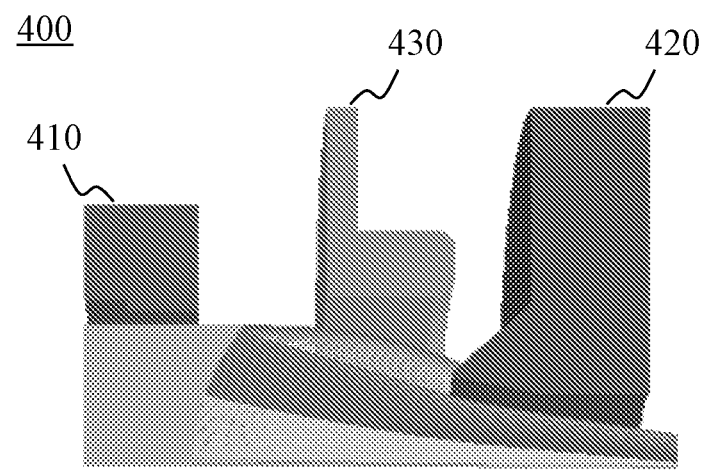
FIG. 4-B

SYSTEM AND METHOD FOR RADIATION THERAPY

CROSS-REFERENCE TO RELATED APPLICATIONS

This application is a continuation of International Application No. PCT/CN2019/092118 field on Jun. 20, 2019, the contents of which are hereby incorporated by reference.

TECHNICAL FIELD

The present disclosure generally relates to systems and methods for radiation therapy, and more particularly, to systems and methods involving an electron injection system configured to allow an adjustment of structure and/or operation parameters.

BACKGROUND

Radiation therapy is widely used in cancer therapy and is also indicated for several other health conditions. Conventionally, a radiation therapy treatment plan (also referred to herein as a treatment plan) for a patient is generated before treatment starts. Different treatment plans for different patients may require different parameters. For example, different parameters of electron beams may be required in different treatment plans. Besides, a radiation therapy system may have different operation modes, such as an imaging mode and a treatment mode. The treatment mode may include a low-energy therapy mode, a medium-energy therapy mode, and/or a high-energy therapy mode. Different treatment modes may have different requirements for electron beams injected into an electron gun. Thus, it may be desirable to develop systems and methods for allowing an adjustment of parameters of an electron injector so that desired electron beams may be produced to satisfy different operation modes.

SUMMARY

In a first aspect of the present disclosure, a system for injecting an electron beam to an accelerator is provided. The system may include a cathode, an anode, and a modulation electrode. The cathode, for generating the electron beam, may have a first electrical potential. The anode may have a second electrical potential. The modulation electrode, located between the cathode and the anode, may be configured to adjust at least one parameter of the electron beam. The at least one parameter of the electron beam may include at least one transverse parameter of the electron beam.

In some embodiments, the at least one transverse parameter of the electron beam may include a Twiss parameter of the electron beam.

In some embodiments, the modulation electrode may be configured to adjust a potential distribution between the cathode and the anode to control a trajectory of the electron beam.

In some embodiments, the system may include a controller configured to apply a third electrical potential to the modulation electrode based on the at least one transverse parameter to adjust the potential distribution between the cathode and the anode.

In some embodiments, the at least one transverse parameter may include at least one of a first parameter or a second parameter. The third electrical potential may be applied based on at least one of the first parameter or the second parameter.

In some embodiments, the first parameter may be a Twiss parameter $\beta$ related to a transverse dimension of the electron beam, and the second parameter may be a Twiss parameter $\gamma$ related to a divergence angle of the electron beam in a transverse direction.

In some embodiments, a first electric field with a first electric field intensity may be generated based on the first electrical potential and the third electrical potential, and a second electric field with a second electric field intensity may be generated based on the second electrical potential and the third electrical potential.

In some embodiments, the first parameter may decrease when the first electric field intensity is smaller than the second electric field intensity.

In some embodiments, the second parameter may increase when the first electric field intensity is smaller than the second electric field intensity.

In some embodiments, the modulation electrode may be configured to control the trajectory of the electron beam by generating a magnetic field between the cathode and the anode based on the at least one transverse parameter.

In some embodiments, the magnetic field may be a solenoid magnetic field.

In some embodiments, the system may include a grid configured to control a beam current of the cathode.

In a second aspect of the present disclosure, a system for injecting an electron beam to an accelerator is provided. The system may include a cathode, an anode, and a modulation electrode. The cathode, for generating the electron beam, may have a first electrical potential. The anode may have a second electrical potential. The modulation electrode, located between the cathode and the anode, may be configured to adjust a profile of the electron beam by controlling a trajectory of the electron beam.

In some embodiments, the profile of the electron beam may be adjusted by adjusting at least one transverse parameter of the electron beam.

In some embodiments, the profile of the electron beam may be adjusted by controlling a potential distribution between the cathode and the anode.

In some embodiments, the potential distribution between the cathode and the anode may be controlled by applying a voltage power supply to the modulation electrode.

In some embodiments, the profile of the electron beam may be adjusted by controlling a magnetic field between the cathode and the anode.

In some embodiments, the modulation electrode may be a magnet.

In some embodiments, at least one of the potential distribution between the cathode and the anode or the magnetic field between the cathode and the anode may be adjusted based on the at least one transverse parameter of the electron beam.

In a third aspect of the present disclosure, a method for adjusting a parameter of the electron beam injected to an accelerator is provided. The method may include following operations. The method may include providing a cathode, for generating the electron beam, having a first electrical potential. The method may include providing an anode having a second electrical potential. The method may include providing a modulation electrode, located between the cathode and the anode, configured to adjust at least one parameter of the electron beam. The at least one parameter of the electron beam may include at least one transverse parameter of the electron beam.

In a fourth aspect of the present disclosure, a method for adjusting a parameter of the electron beam injected to an accelerator is provided. The method may include following operations. The method may include providing a cathode, for generating the electron beam, having a first electrical potential. The method may include providing an anode having a second electrical potential. The method may include providing a modulation electrode, located between the cathode and the anode, configured to adjust a profile of the electron beam by controlling a trajectory of the electron beam.

In a fifth aspect of the present disclosure, a non-transitory computer readable medium may include at least one set of instructions. When executed by at least one processor of a computing device, the at least one set of instructions may cause the at least one processor to effectuate a method. The method may include providing a cathode, for generating the electron beam, having a first electrical potential. The method may include providing an anode having a second electrical potential. The method may include providing a modulation electrode, located between the cathode and the anode, configured to adjust at least one parameter of the electron beam. The at least one parameter of the electron beam may include at least one transverse parameter of the electron beam.

In a sixth aspect of the present disclosure, a non-transitory computer readable medium may include at least one set of instructions. When executed by at least one processor of a computing device, the at least one set of instructions may cause the at least one processor to effectuate a method. The method may include providing a cathode, for generating the electron beam, having a first electrical potential. The method may include providing an anode having a second electrical potential. The method may include providing a modulation electrode, located between the cathode and the anode, configured to adjust a profile of the electron beam by controlling a trajectory of the electron beam.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIGS. 4-A and 4-B are schematic diagrams illustrating an exemplary electron injector and electron beams in the electron injector according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 2:
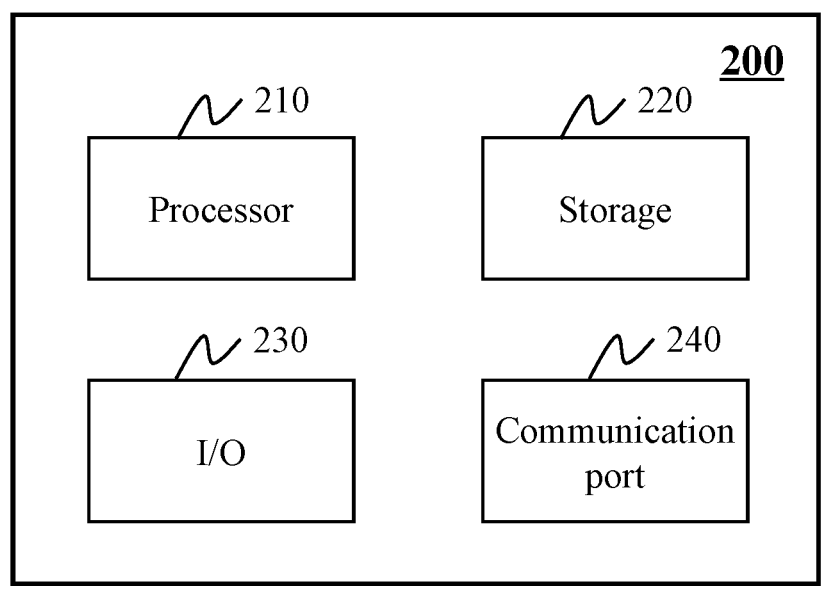
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/ blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Provided herein are systems and components for non-invasive imaging and/or treatment, such as for disease diagnosis, treatment or research purposes. In some embodiments, the system may be a radiation therapy system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy. The term "image" used in this disclosure may refer to a 2D image, a 3D image, or a 4D image. In some embodiments, the term "image" may refer to an image of a region of interest (ROI) of a patient. The term "region of interest" or "ROI" used in this disclosure may refer to a part of an image along a line, in two spatial dimensions, in three spatial dimensions, or any one of the above as it evolves as a function of time. The image may be a CT image, an Electronic Portal Image Device (EPID) image, a fluoroscopy image, an ultrasound image, a positron emission tomography (PET) image, or a magnetic resonance image.

Some embodiments of the present disclosure relate to systems and methods involving an electron injection system configured to allow an adjustment of structure and/or operation parameters for imaging, planning and/or performing radiation therapy. In some embodiments, the electron injection system may include an electron injector. The electron injector may include a modulation electrode. The modulation electrode may be adjusted so that a same electron injector may produce desired electron beams to satisfy different operations on the system for imaging or radiation therapy, e.g., different imaging procedures.

Figure 1:
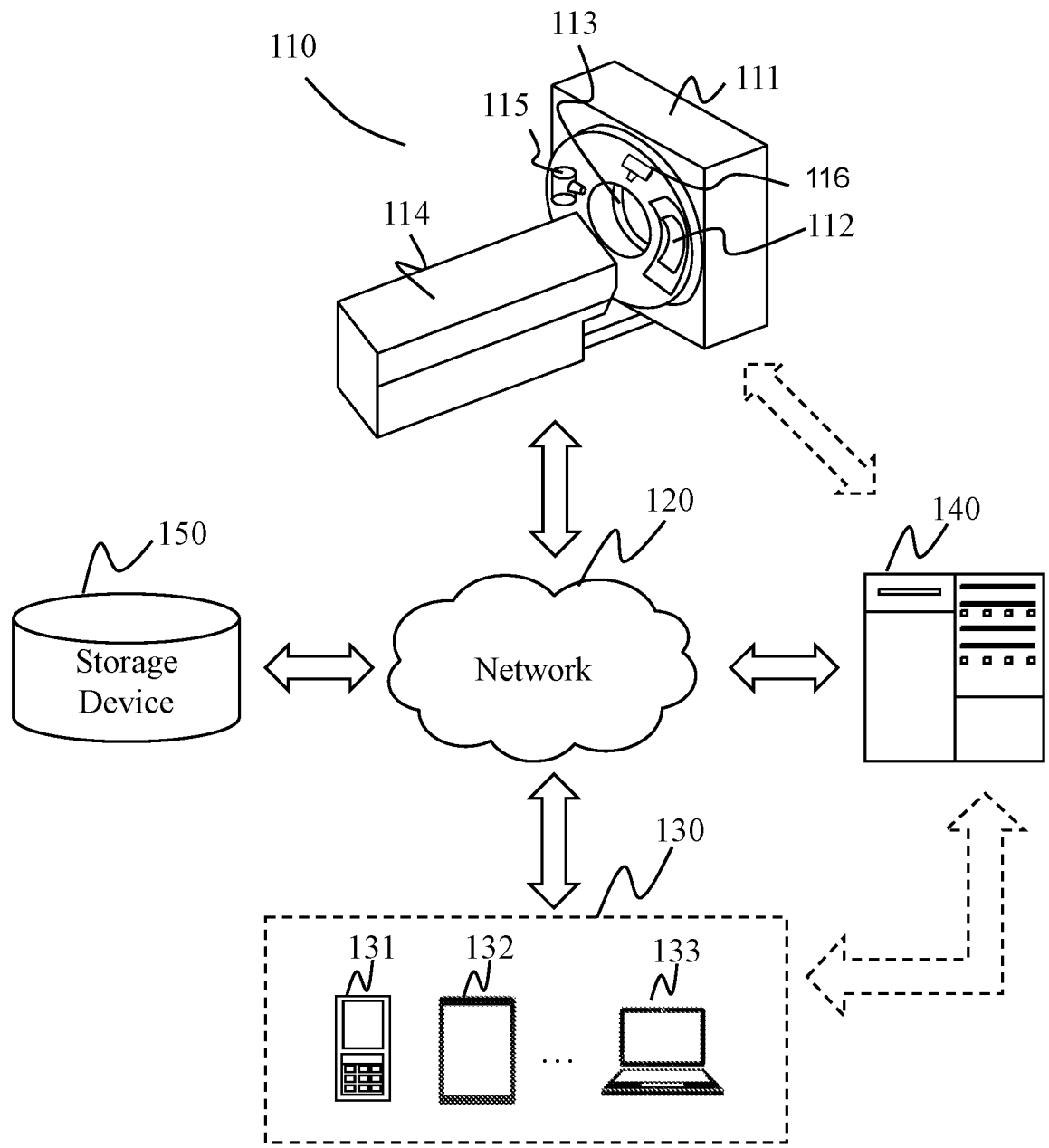
FIG. 1 is a schematic diagram illustrating an exemplary radiation therapy system according to some embodiments of the present disclosure.

FIG. 1 is a schematic diagram illustrating an exemplary radiation therapy system 100 according to some embodiments of the present disclosure. The radiation therapy system 100 may include a radiation delivery device 110, a network 120, one or more terminals 130, a processing device 140, and a storage device 150.

In some embodiments, the radiation delivery device 110 may include an imaging component, a treatment component, a gantry 111, a table 114, an imaged region 113, or the like. In some embodiments, the imaging component may include an imaging-radiation source 115, a detector 112, or the like. The treatment component may include a treatment radiation source 116, or the like. The gantry 111 may be configured to accommodate the imaging component and the treatment component, such as the imaging-radiation source 115, the detector 112, and the treatment radiation source 116. A subject may be placed on the table 114 for treatment and/or scan.

The imaging component may generate an image of the subject before, during and/or after a treatment fraction. The imaging component may include a computed tomography (CT) component, an ultrasound imaging component, a fluoroscopy imaging component, a magnetic resonance imaging (MRI) component, a single photon emission computed tomography (SPECT) component, a positron emission tomography (PET) component, or the like, or any combination thereof.

The imaging-radiation source 115 may emit radiation toward the subject. The detector 112 may detect radiation (e.g., x-ray photons, gamma-ray photons) transmitted from the imaged region 113. In some embodiments, the detector 112 may include one or more detector units. The detector units may include a scintillation detector (e.g., a cesium iodide detector, a gadolinium oxysulfide detector), a gas detector, etc. The detector unit may include a single-row detector and/or a multi-rows detector.

The treatment component may deliver radiation treatment to the subject. The treatment radiation source 116 may emit treatment radiations towards the subject.

In some embodiments, the radiation delivery device 110 may include two gantries that house the imaging component and the treatment component, respectively. The imaging component (e.g., the imaging-radiation source 115 and the detector 112) and the corresponding gantry may be spaced by a distance from the treatment component (e.g., the treatment radiation source 116) and the corresponding gantry. In some embodiments, the corresponding gantry of the imaging component and the corresponding gantry of the imaging component may have collinear bore. For example, the bore of the imaging component gantry and bore of the treatment component gantry may share an axis of rotation. The subject may be positioned in different positions in the table 114 for imaging and treatment. In some embodiments, the imaging-radiation source 115 and the treatment radiation source 116 may be integrated as one radiation source to image and/or treat the subject. In some embodiments, the imaging component may be omitted. The treatment radiation source 116 may be configured to image and treat the subject.

In some embodiments, the imaging radiation source 115 and/or the treatment radiation source 116 may at least include an electron generator (also refers to a cathode) and an accelerator. The electron generator may be configured to generate an electron beam. The accelerator may accelerate electrons of the electron beam. The electron beam after acceleration may hit a target to generate radiation rays thereby. In some embodiments, the electron beam after acceleration may be used to treat the subject without hitting the target.

The network 120 may include any suitable network that can facilitate the exchange of information and/or data for the radiation therapy system 100. In some embodiments, one or more components of the radiation therapy system 100 (e.g., the radiation delivery device 110, the terminal 130, the processing device 140, the storage device 150, etc.) may communicate information and/or data with one or more other components of the radiation therapy system 100 via the network 120. For example, the processing device 140 may obtain image data from the radiation delivery device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

Figure 3:
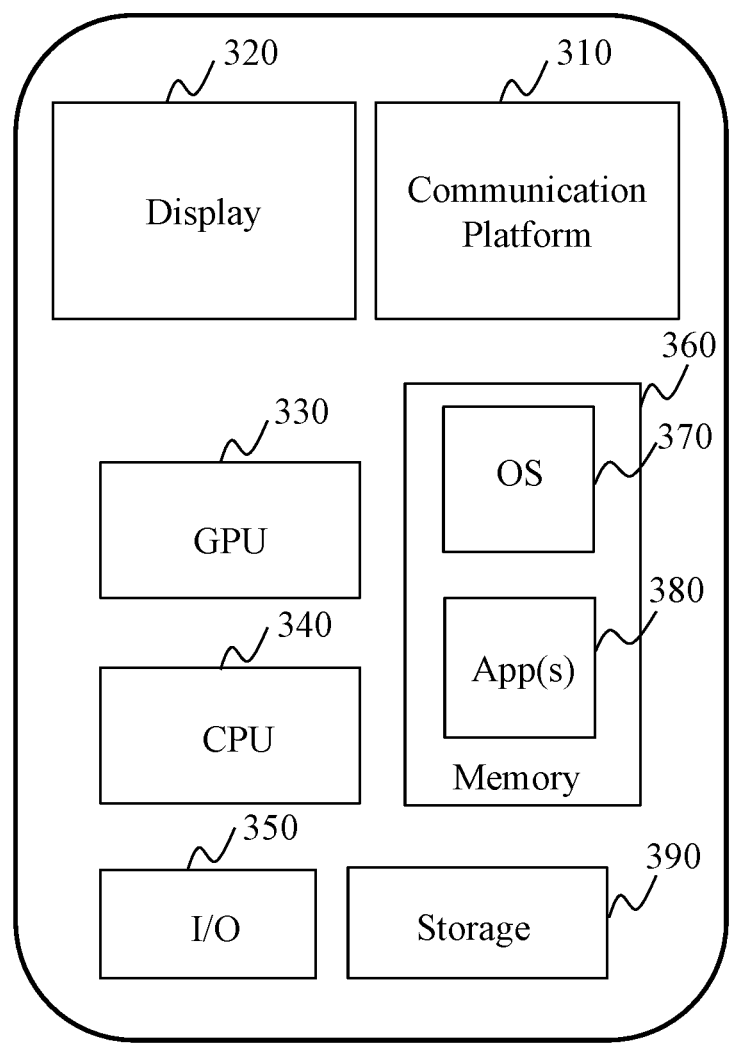
FIG. 3 is a schematic diagram illustrating hardware and/or software components of an exemplary mobile device according to some embodiments of the present disclosure.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™ etc. In some embodiments, the terminal(s) 130 may be part of the processing device 140.

The processing device 140 may process data and/or information obtained from the radiation delivery device 110, the terminal 130, and/or the storage device 150. In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the radiation therapy system 100 (e.g., the processing device 140, the terminal 130). One or more components of the radiation therapy system 100 may access the data or instructions stored in the storage device 150 via the network 120. In some embodiments, the storage device 150 may be directly connected to or communicate with one or more other components of the radiation therapy system 100 (e.g., the processing device 140, the terminal 130). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, storage 220, an input/output (I/O) 230, and a communication port 240.

The processor 210 may execute computer instructions (e.g., program code) and perform functions of the processing device 140 in accordance with techniques described herein.

The computer instructions may include, for example, routines, programs, objects, components, data structures, procedures, modules, and functions, which perform particular functions described herein. For example, the processor 210 may process image data obtained from the radiation delivery device 110, the terminal 130, the storage device 150, and/or any other component of the radiation therapy system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is illustrated in the computing device 200 in FIG. 2. However, it should be noted that the computing device 200 in the present disclosure may also include multiple processors, and thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiation delivery device 110, the terminal 130, the storage device 150, and/or any other component of the radiation therapy system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip drive, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation therapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

FIGS. 4-A and 4-B illustrate an exemplary electron injector and an electron beam in the electron injector according to some embodiments of the present disclosure. The electron injector 400 may be implemented on the imaging radiation source 115 and/or the treatment radiation source 116. The electron injector 400 may be configured to generate an electron beam.

As shown in FIG. 4-A and FIG. 4-B, the electron injector 400 may include a cathode 410, an anode 420, and a modulation electrode 430.

In some embodiments, the cathode 410 may be configured to generate electrons. For example, the cathode 410 may be a thermionic cathode emitter, as of the dispenser or oxide coated nickel type. The cathode 410 may have a cathode emitting surface for supplying copious electron emission when heated to its operating temperature. In some embodiments, the cathode emitting surface may be a spherically concave surface. The cathode 410 may be heated via a heating element disposed in a heat exchange relation with the cathode 410. In some embodiments, the heating element may include one or more filaments. A filament power supply may supply electrical power to the heating element. The cathode 410 may be directly or indirectly heated by the one or more filaments powered by the filament power supply. The heating of the cathode 410 may cause the emission of electrons from the surface of the cathode 410. In general, as the temperature of the cathode emitting surface (or referred to as the surface for brevity) of the cathode 410 increases, the number (or count) of electrons emitted increases. In some embodiment, the filament power supply and filaments may be operated to heat the cathode 410 to a temperature of approximately 800-1500° C., depending on the application of radiation generated therefrom. The axis of revolution of the spherically concave cathode emitting surface may be axially aligned with a central aperture in the anode 420 which is axially spaced from the cathode. In some embodiments, the electron injector 400 may be a Pierce type electron injector to provide a convergent flow electron beam that is projected through the aperture in the anode in a substantially non-intercepting manner.

The anode 420 may be set at an electrical potential (also refers to second electrical potential) greater than the electrical potential of the cathode 410 (also refers to first electrical potential). The high electrical potential of the anode 420 may be achieved by applying a high negative voltage power supply to the cathode 410. The potential difference (also refers to cathode-to-anode voltage) of the cathode 410 and the anode 420 may form an electric field. Electrons emitted from the cathode 410 may be accelerated and be attracted towards the anode 420 as a result of the potential difference. The anode 420 may have an aperture through which the accelerated electron beam may pass and further be accelerated by an accelerator. The anode 420 may be any of a variety of different types of anodes suitable for an electron injector. For instance, the anode 420 may be configured to generate an electron beam of a desired shape and concentration for delivery into the accelerator. The shape and placement of the aperture on the anode 420 may have a direct effect on the shape and concentration of the electron beam. A variety of different shapes of the anode 420 may be used, depending on a desired beam shape and/or concentration.

The modulation electrode 430 may be configured to control a profile of the electron beam by controlling a trajectory of the electron beam based on one or more transverse parameters. In some embodiments, the trajectory of the electron beam may be affected by an electric field and/or a magnetic field between the cathode 410 and the anode 420. The modulation electrode 430 may control the profile of the electron beam by adjusting the electric field and/or the magnetic field between the cathode 410 and the anode 420. In some embodiments, the profile of the electron beam may include a transverse distribution of the electron beam along a transverse direction. The transverse direction of the electron beam may be perpendicular to a propagation direction (e.g., an axial direction) of the electron beam. Accordingly, the modulation electrode 430 may control the profile of the electron beam by adjusting the transverse distribution of the electron beam based on the one or more transverse parameters.

The modulation electrode 430 may be located between the cathode 410 and the anode 420. The modulation electrode 430 may have any suitable structure. For example, the modulation electrode 430 may have a stepped ring structure with an aperture for the accelerated electron beam to pass through, as shown in FIGS. 4A and 4B. The stepped ring structure of the modulation electrode 430 may facilitate a connection between the modulation electrode 430 and one or more other components of the radiation therapy system 100. For example, the one or more other components may be welded to a convex part of the modulation electrode 430. In some embodiments, the modulation electrode 430 may be made of a conductive material. For example, the modulation electrode 430 may be made of iron, copper, or the like, or an alloy thereof, or any combination thereof.

In some embodiments, the modulation electrode 430 may be controlled by a controller. The controller may control the electric field and/or the magnetic field between the cathode 410 and the anode 420 to control the trajectory of the electron beam.

In some embodiments, the controller may control the electrical potential applied on the modulation electrode 430 to adjust the profile of the electron beam. For example, the controller may apply a third electrical potential to the modulation electrode 430 based on the one or more transverse parameters to adjust the potential distribution between the cathode 410 and the anode 420. The one or more transverse parameters may include at least one Twiss parameter, such as a first parameter ($\beta$) and a second parameter ($\gamma$). The first parameter may be related to a transverse dimension of the electron beam in the transverse direction. The second parameter may be related to a divergence angle of the electron beam in the transverse direction. In some embodiments, a first electric field with a first electric field intensity may be generated based on the first electrical potential and the third electrical potential. A second electric field with a second electric field intensity may be generated based on the second electrical potential and the third electrical potential. When the first electric field intensity is smaller than the second electric field intensity, the first parameter ($\beta$) may decrease and the second parameter ($\gamma$) may increase. Thus, the controller may control the electrical potential applied on the modulation electrode 430 to change the Twiss parameters of the electron beam, and in turn the profile of the electron beam.

In some embodiments, for a certain imaging and/or treatment procedure, the desired radiation may be estimated, which means not only the certain the beam current, but also proper transverse parameters of the electron beam. The controller may cause an electrical potential to be applied on the modulation electrode 430 to generate an electron beam of a desired profile. The electrical potential may be determined based on the transverse parameters of the electron beam.

Figure 7:
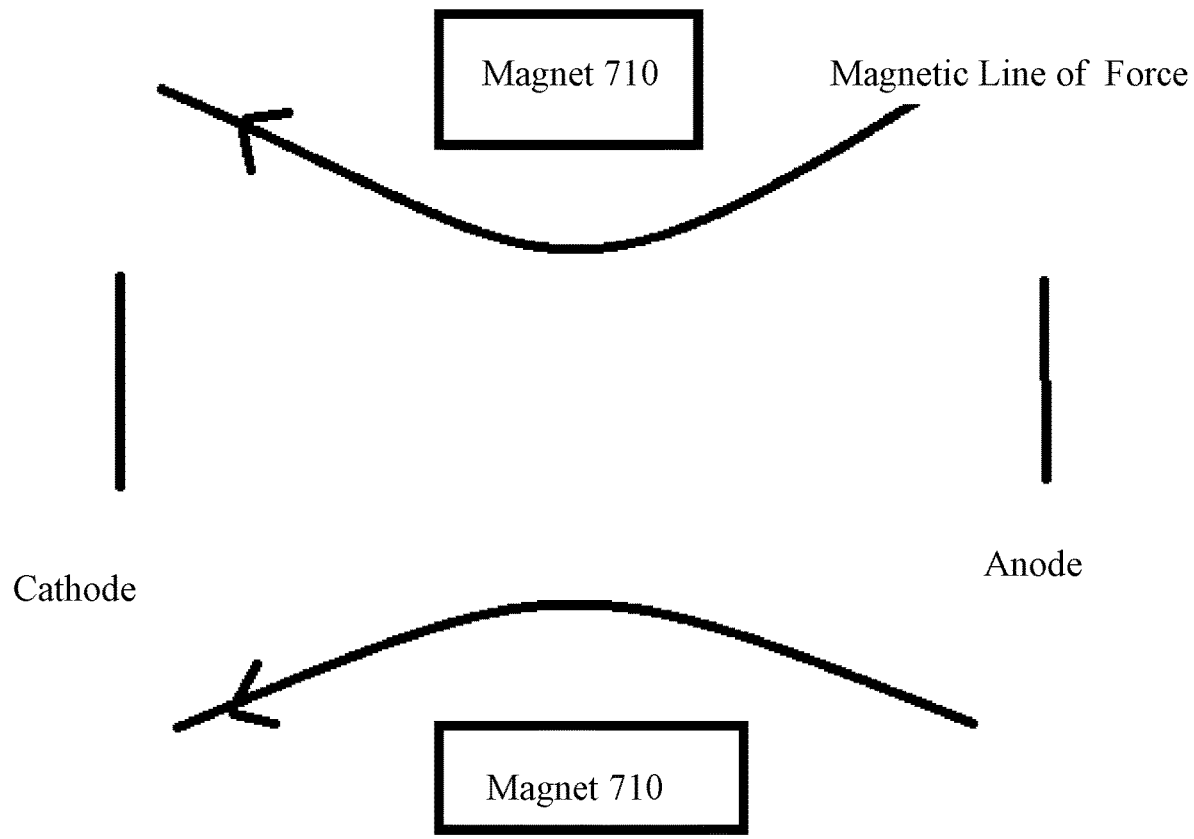
FIG. 7 is a schematic diagram illustrating an exemplary magnetic field according to some embodiments of the present disclosure.

In some embodiments, the modulation electrode 430 may be controlled by a controller to generate a magnetic field between the cathode 410 and the anode 420. In some embodiments, the modulation electrode 430 may be a magnet (e.g., a magnet 710 as illustrated in FIG. 7). For example, the modulation electrode 430 may be a permanent magnet, a coil, or the like. In some embodiments, the magnetic field may be a solenoid magnetic field, as shown in FIG. 7. The controller may control the modulation electrode 430 to adjust the magnetic field between the cathode 410 and the anode 420 in order to adjust the trajectory of the electron beam generated by the cathode 410, so that an electron beam of a desired profile may be generated.

It should be noted that the above descriptions of the electron injector 400 is provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the electron injector 400 may include one or more other components. For example, two or more modulation electrodes may be included in the electron injector 400 to generate an eligible electron beam in order to produce the desired radiations for a certain imaging and/or treatment. In some embodiments, two or more components in the electron injector 400 may be combined into a single component. For example, the filament and the cathode 410 may be integrated into a single component.

Figure 5:
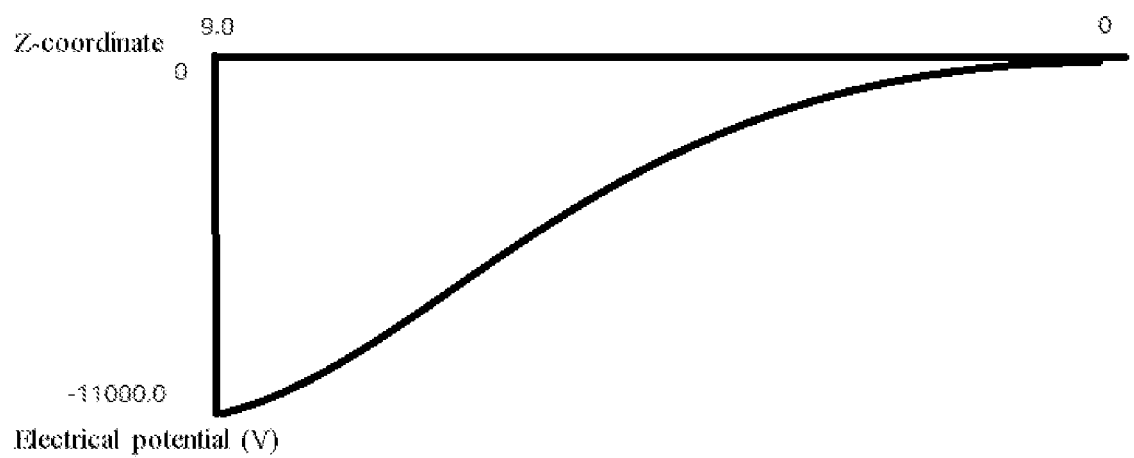
FIG. 5 is a schematic diagram illustrating a relationship between the electrical potential and a position along the axis of the electron beam.

FIG. 5 is a schematic diagram illustrating a relationship between the electrical potential and a position along the axis of the electron beam. The position along the axis of the electron beam may be represented by a Z-coordinate, while the X-coordinate and Y-coordinate may be zero. The origin of the axis is at anode, and the positive direction of the axis is from the anode to the cathode.

As shown in FIG. 5, at the position along the axis of the electron beam with a Z-coordinate of zero (0), the electrical potential may be zero, which means the anode 420 may be set at an electrical potential of zero volts (0V). The electrical potential of the position along the axis of the electron beam with a maximum Z-coordinate (e.g., 9 as illustrated in FIG. 5) which approaches the cathode 410 may be approximately −12,000 volts. The high electrical potential of the anode 420 may be achieved by applying a high negative voltage power supply to the cathode 410. According to the relationship curve of the electrical potential and the position along the axis of the electron beam represented by a Z-coordinate, when the Z-coordinate increases, the electrical potential of the position along the axis of the electron beam may decrease. The slope of the relationship curve may increase and then decreases, which means the first intensity of the first electric field between the cathode 410 and the modulation electrode 430 is larger than the second intensity of the second electric field between the modulation electrode 430 and the anode 420.

It should be noted that the above descriptions of relationship between the electrical potential and a position in the axis of the electron beam is provided for the purposes of illustration, and not intended to limit the scope of the present disclosure. For persons having ordinary skills in the art, various modifications and changes in the forms and details of the application of the above method and system may occur without departing from the principles of the present disclosure. For example, when the first intensity of the first electric field between the cathode 410 and the modulation electrode 430 is less than the second intensity of the second electric field between the modulation electrode 430 and the anode 420, the slope of the relationship curve may decrease and then increase.

Figure 6:
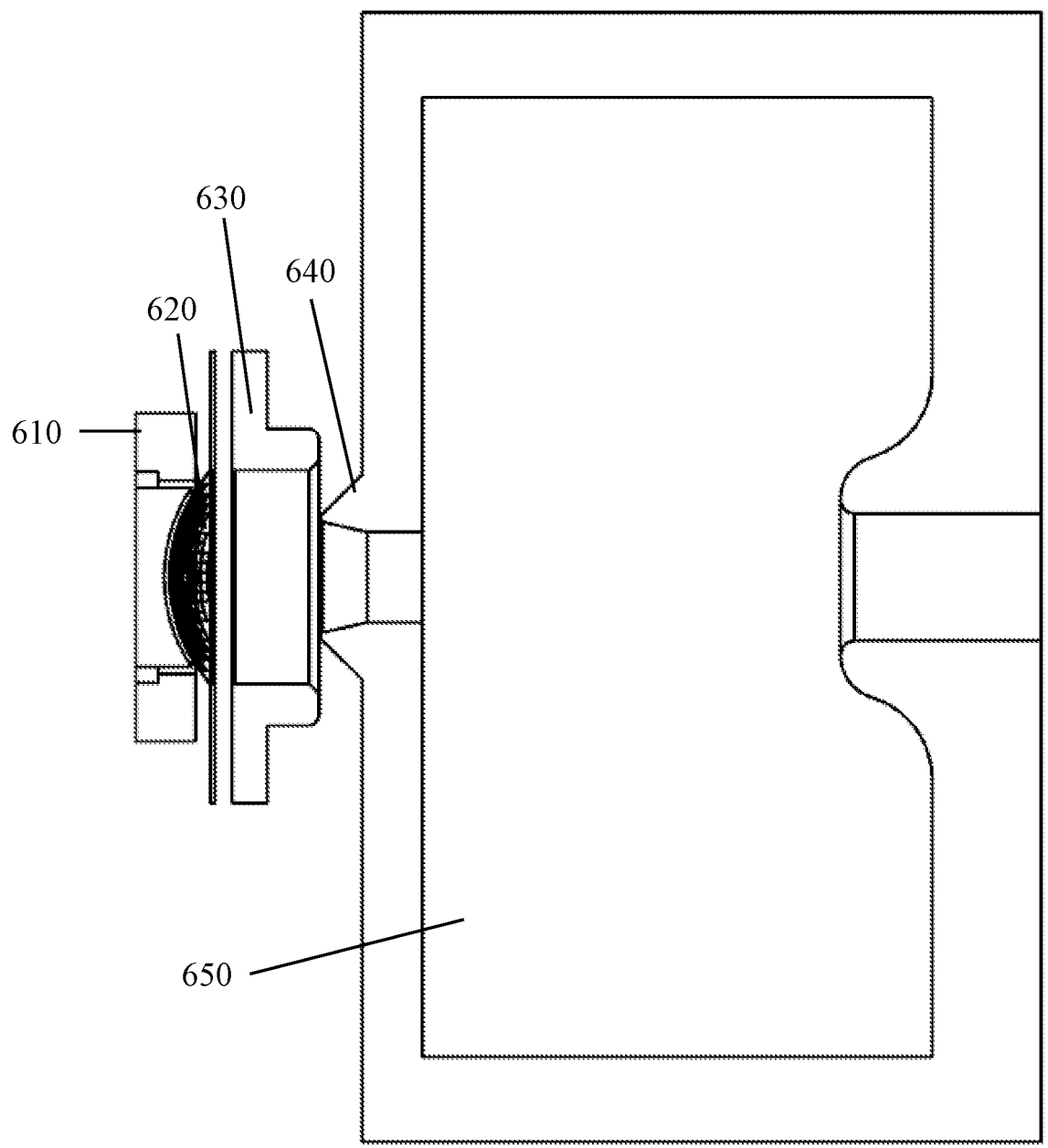
FIG. 6 is a schematic diagram illustrating a cross-section view of components of an exemplary accelerator system according to some embodiments of the present disclosure.

FIG. 6 is a schematic diagram illustrating in a cross-section view of components of an exemplary accelerator system according to some embodiments of the present disclosure. As shown in FIG. 6, the accelerator system 600 may include an electron injector and an accelerator 650. The electron injector may include a cathode 610, a grid 620, and a modulation electrode 630. The accelerator structure may include an anode 640 and an accelerator 650. An electron beam may be generated in the cathode 610 and accelerated because of the electric field while traveling toward the grid 620, the modulation electrode 630, and the anode 640. Further, the electron beam passes through a central aperture in the anode 640 and enters into the accelerator 650 for further acceleration. Electrons of the electron beam may have enough energy to produce radiation of a desired dose level for a certain imaging and/or treatment procedure.

The cathode 610 of the accelerator system 600 may be configured to generate electrons. The cathode 610 may be the same as or similar to the cathode 410, the description of which is not repeated here.

The grid 620, in the accelerator system 600, may be configured to control the beam current of the cathode 610. In some embodiments, the cathode emitting surface of the cathode 610 may have a shape of a spherical concave, and the grid 620 may have a shape of a spherical concave corresponding to the cathode emitting surface of the cathode 610. The grid 620 may include a plurality of apertures. The grid 620 may be made of molybdenum, tungsten, or the like. The material of the grid 620 may be disposed closely overlaying the concave cathode emitting surface. In some embodiments, the grid 620 may be supported at its outer periphery via a support structure disposed on the cathode 610. In some embodiments, the support structure may be a cylindrical structure. The grid 620 may be thermally and electrically insulated from the cathode 610. A grid bias supply may supply a DC negative grid bias to the grid 620 so that the grid 620 is normally biased off, i.e., a beam current (e.g., the current of the flow of electrons) is off. A grid pulser may be serially connected with a grid RF source for applying a positive pulse of a desired magnitude such that the grid 620 is pulsed positive relative to the cathode 610 for pulsing the beam current through the anode 640.

The modulation electrode 630, in the accelerator system 600, may be configured to control a profile of the electron beam by controlling a trajectory of the electron beam. The modulation electrode 630 may be located between the grid 620 and the anode 640.

In some embodiments, the modulation electrode 630 may be controlled by a controller, which may apply an electrical potential (also referred to as third electrical potential) to the modulation electrode 630. The controller may control, through the modulation electrode 630, a potential distribution between the cathode 610 and the anode 640 which in turn may influence the trajectory of the electron beam. For example, the electrical potential applied on the modulation electrode 430 may be adjusted. Then the one or more transverse parameters of the electron beam may change accordingly. The one or more transverse parameters may include Twiss parameters, such as a first parameter ($\beta$) and a second parameter ($\gamma$). For example, a first electric field with a first electric field intensity may be generated based on the first electrical potential and the third electrical potential. A second electric field with a second electric field intensity may be generated based on the second electrical potential and the third electrical potential. When the first electric field intensity is smaller than the second electric field intensity, the first parameter ($\beta$) may decrease and the second parameter ($\gamma$) may increase. Thus, the controller may control the electrical potential applied on the modulation electrode 630 to change the Twiss parameters, further the profile of the electron beam. In some embodiments, for a certain imaging and/or treatment procedure, a desired radiation may be estimated, which means not only the certain the beam current, but also the proper transverse parameters of the electron beam. The controller may control the electrical potential to be applied on the modulation electrode 630 based on the proper transverse parameters to generate radiation of a desired dose level.

In some embodiments, the modulation electrode 630 may be controlled by a controller to form a magnetic field between the cathode 610 and the anode 640. The controller may control the modulation electrode 630 to adjust the magnetic field between the cathode 610 and the anode 640 in order to adjust the trajectory of the electron beam generated by the cathode 610, so that an electron beam of a desired profile may be generated.

The anode 640 of the accelerator system 600 may be set at an electrical potential (also referred to as the second electrical potential) greater than the electrical potential of the cathode 610 (also referred to as the first electrical potential). The high electrical potential of the anode 420 may be achieved by applying a high negative voltage power supply to the cathode 410. The anode 640 may be the same as or similar to the anode 420, the description of which is not repeated here.

The accelerator 650 of the accelerator system 600 may be configured to accelerate the electron beam. As shown in FIG. 6, the electron beam may enter the accelerator 650 through the aperture on the anode 640. The electrons may have been accelerated by the electric fields between the cathode 610 and the anode 640. The accelerator 650 may include a plurality of linked accelerating cells (not illustrated), through which an electron flow path is defined. A microwave signal may be transmitted along the accelerator 650, resulting in an electromagnetic standing wave. As electrons pass through the accelerator 650 at relativistic speeds, the timing of microwaves and electron pulses may be controlled such that the electrons "see" a positive accelerating electrical potential in each cell.

It should be noted that the above descriptions of the accelerator system 600 is provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the accelerator system 600 may include one or more other components. In some embodiments, two or more components in the accelerator system 600 may form one component. However, those variations and modifications also fall within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system for injecting an electron beam to an accelerator, comprising:
a cathode, for generating the electron beam, having a first electrical potential;
an anode having a second electrical potential; and
a modulation electrode, located between the cathode and the anode, configured to adjust at least one parameter of the electron beam by adjusting a magnetic field or a potential distribution between the cathode and the anode, wherein the at least one parameter of the electron beam includes at least one transverse parameter of the electron beam.

2. The system of claim 1, wherein the at least one transverse parameter of the electron beam includes a Twiss parameter of the electron beam.

3. The system of claim 1, wherein the modulation electrode is configured to control a trajectory of the electron beam by adjusting the at least one parameter of the electron beam.

4. The system of claim 3, further comprising:
a controller configured to apply a third electrical potential to the modulation electrode based on the at least one transverse parameter to adjust the potential distribution between the cathode and the anode.

5. The system of claim 4, wherein the at least one transverse parameter includes at least one of a first parameter or a second parameter, and the third electrical potential is applied based on at least one of the first parameter or the second parameter.

6. The system of claim 5, wherein the first parameter is a Twiss parameter $\beta$ related to a transverse dimension of the electron beam, and the second parameter is a Twiss parameter $\gamma$ related to a divergence angle of the electron beam in a transverse direction.

7. The system of claim 5, wherein a first electric field with a first electric field intensity is generated based on the first electrical potential and the third electrical potential, and a second electric field with a second electric field intensity is generated based on the second electrical potential and the third electrical potential.

8. The system of claim 7, wherein the first parameter decreases when the first electric field intensity is smaller than the second electric field intensity.

9. The system of claim 7, wherein the second parameter increases when the first electric field intensity is smaller than the second electric field intensity.

10. The system of claim 1, wherein the magnetic field is a solenoid magnetic field.

11. The system of claim 1, further comprising:
a grid, configured to control a beam current of the cathode.

12. A system for injecting an electron beam to an accelerator, comprising:
a cathode, for generating the electron beam, having a first electrical potential;
an anode having a second electrical potential; and
a modulation electrode, located between the cathode and the anode, configured to adjust a profile of the electron beam by controlling a trajectory of the electron beam.

13. The system of claim 12, wherein the profile of the electron beam is adjusted by adjusting at least one transverse parameter of the electron beam.

14. The system of claim 12, wherein the profile of the electron beam is adjusted by controlling a potential distribution between the cathode and the anode.

15. The system of claim 14, wherein the potential distribution between the cathode and the anode is controlled by applying a voltage power supply to the modulation electrode.

16. The system of claim 14, wherein at least one of the potential distribution between the cathode and the anode or a magnetic field between the cathode and the anode is adjusted based on at least one transverse parameter of the electron beam.

17. The system of claim 12, wherein the profile of the electron beam is adjusted by controlling a magnetic field between the cathode and the anode.

18. The system of claim 17, wherein the modulation electrode is a magnet.

19. A method for adjusting a parameter of an electron beam injected to an accelerator, comprising:
   providing a cathode, for generating the electron beam, having a first electrical potential;
   providing an anode having a second electrical potential; and
   providing a modulation electrode, located between the cathode and the anode, configured to adjust at least one parameter of the electron beam by adjusting a magnetic field or a potential distribution between the cathode and the anode, wherein the at least one parameter of the electron beam includes at least one transverse parameter of the electron beam.

* * * * *